United States Patent [19]

Dahms

[11] 4,111,784

[45] Sep. 5, 1978

[54] APPARATUS FOR ELECTROPHORESIS

[76] Inventor: Harald Dahms, 22 Lakeview Rd., Ossining, N.Y. 10562

[21] Appl. No.: 797,903

[22] Filed: May 18, 1977

Related U.S. Application Data

[63] Continuation of Ser. No. 658,372, Feb. 17, 1976, abandoned, which is a continuation of Ser. No. 566,245, Apr. 19, 1975, abandoned, which is a continuation of Ser. No. 392,652, Aug. 29, 1973, abandoned, which is a continuation of Ser. No. 122,310, Mar. 9, 1971, abandoned.

[51] Int. Cl.² .................... G01N 27/26; G01N 27/28
[52] U.S. Cl. .................... 204/299 EC; 204/180 G; 204/307
[58] Field of Search .............. 204/299, 180 S, 180 G, 204/301, 300; 23/230 B

[56] References Cited

U.S. PATENT DOCUMENTS

| 3,399,127 | 8/1968  | Rand et al. | 204/180 G |
| 3,523,863 | 8/1970  | Juhos       | 204/299 X |
| 3,554,894 | 1/1971  | Zemel       | 204/299   |
| 3,844,918 | 10/1974 | Cawley      | 204/180 G |

Primary Examiner—Arthur C. Prescott

[57] ABSTRACT

A plate for use in electrophoresis, comprising a membrane coated with a layer of an electrophoretic medium such as agarose gel. The membrane is bonded to a supporting sheet having cutouts in which the electrophoresis is performed. A transport apparatus moves the plates through an electrophoresis bath into an optical scanning densitometer.

25 Claims, 8 Drawing Figures

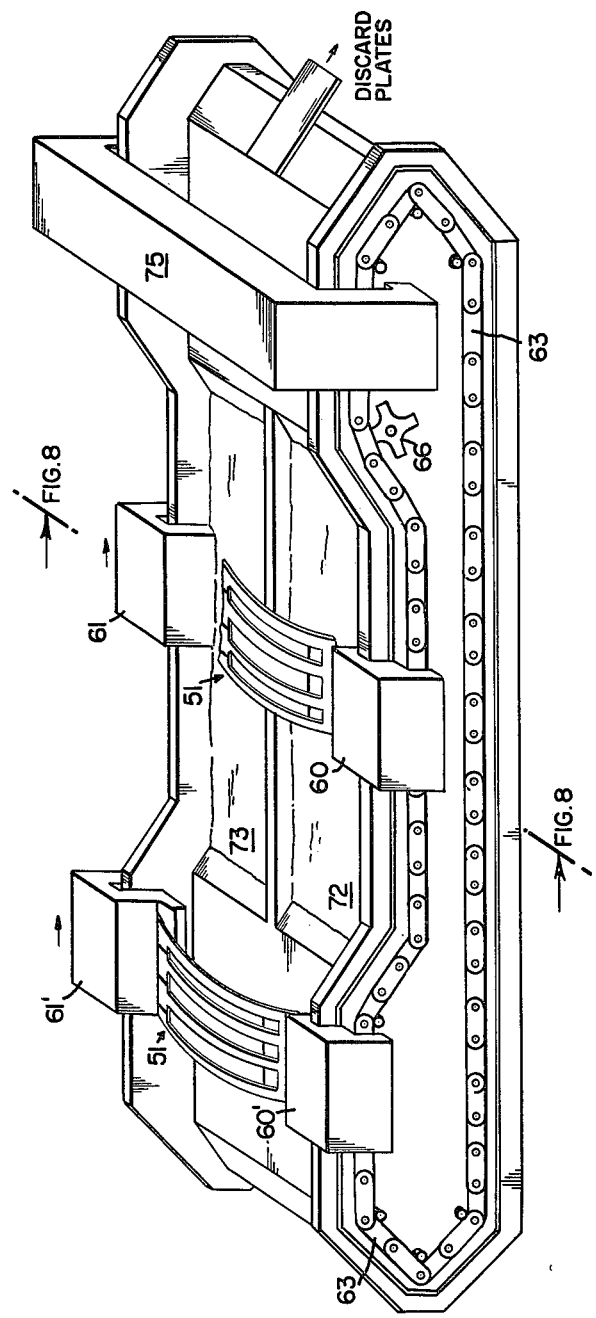

APPARATUS FOR ELECTROPHORESIS

This is a continuation of application Ser. No. 658,372 filed Feb. 17, 1976, and now abandoned, which is a continuation of application Ser. No. 566,245, filed Apr. 19, 1975, and now abandoned, which is a continuation of application Ser. No. 392,652 filed Aug. 29, 1973, and now abandoned, which is a continuation of application Ser. No. 122,310 filed Mar. 9, 1971, now abandoned.

This invention relates to electrophoresis and, more particularly, to the use of thin gel films for electrophoresis.

electrophoresis is a well known method for the separation of electrically charged species, utilizing the differences in rate of migration in an electrical field. Electrophoresis is, for example, widely used in the analysis of serum proteins. Most analytical electrophoresis methods use the principle of zone electrophoresis. A thin zone of the sample is applied to the elecrophoretic medium. The electrophoretic migration splits this starting zone into fractional zones. The quantity of protein in each fraction is then determined either by colorimetric or fluorometric methods or by measuring the absorption of ultraviolet light by proteins. It is desirable to perform the electrophoretic separation in a minimum of time with a maximum degree of separation. Electrophoretic separations are currently being performed on a wide variety of electrophoretic media. One class of such electrophoretic media utilizes gel films such as agarose gel films. The use of a thin gel film supported on a plastic base is, for example, described in U.S. Pat. No. 3,479,265. The plastic base supports the agarose film and keeps it in rectangular shape so that it can be easily handled.

I have now found that I obtain improved operating characteristics by using a gel film on an extremely thin and flexible membrane. Such membrane is so flexible and thin that it curls up and wrinkles and cannot be kept in a flat stretched shape when handled. I am providing a frame which is permanently bonded to the membrane to keep the membrane, carrying the gel, stretched and wrinkle-free. The frame may also serve to act as boundary for the gel film. I have found it to be important that the electrophoretic separation is performed where the membrane is not supported by or bonded to the frame. After electrophoresis, the separated fractions may be determined by measuring their absorption of ultraviolet light through the membrane. The electrophoresis plate consisting of the membrane bonded to the frame may be adapted for use in a transport system which moves the plate through an electrophoresis bath into an appartus for measuring the absorption of ultraviolet light.

It is an object of the invention to provide an electrophoresis plate on which electrophoretic separations can be performed with a high degree of separation.

It is another object of the invention to provide an electrophoresis plate on which the separated fractions can be determined by measuring the absorption of ultraviolet light.

It is still another object of the invention to provide a transport apparatus which moves electrophoretic plates through an electrophoretic bath to an optical scanning apparatus.

These and further objects and advantages of the invention will become more apparent upon reference to the following specification and claims and appended drawings wherein:

BRIEF DESCRIPTION OF THE DRAWINGS

FIG. 7 is a view of a transport apparatus to move electrophoresis plates through an electrophoresis bath into an optical densitometer.

DETAILED DESCRIPTION OF THE PREFERRED EMBODIMENTS

Figure 1:
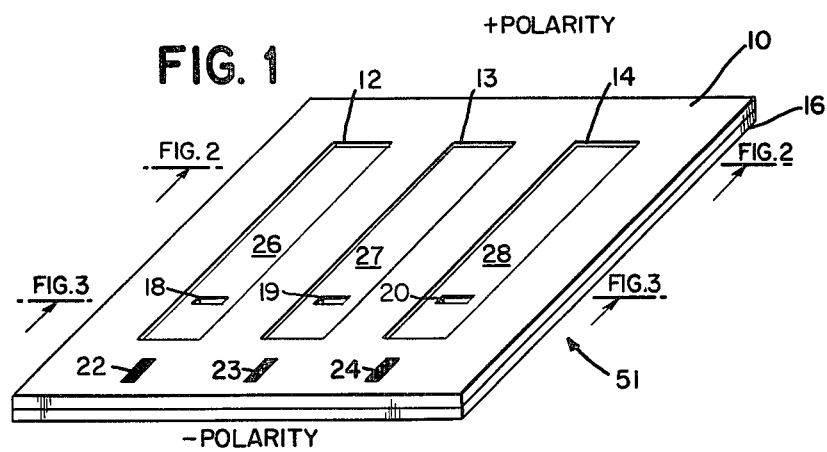
FIG. 1 is a view of a plate for performing electrophoretic separations thereon.

Referring now to FIG. 1, there is shown, generally indicated at 51, a plate for use in electrophoresis. Sheet 10 is bonded to membrane 16. Sheet 10 acts as a frame to stretch membrane 16. Membrane 16 is preferably less than 0.05 mm in thickness and is so thin and flexible that it cannot maintain itself in a flat plane when held on one side. I have used, for example, "Clear Food Wrap 200", sold by Shop-Rite Supermarkets in rolls of 200 feet, 11 ¾ inches wide, having a thickness of 0.008 mm. I have also used "Saran Wrap" made by Dow Chemical Co. in rolls of 100 feet, 11 ¼ inches wide, having a thickness of about 0.015 mm. "Saran" consists mainly of polyvinylidene chloride. It is the generic term for thermoplastic resins obtained by the polymerisation of vinylidene chloride with lesser amounts of other unsaturated compounds. Sheet 10 has rectangular cutouts 12, 13, and 14. Sheet 10 is typically 0.25 mm in thickness. A typical length of each cutout is 75 mm, the width 10 mm. I have used materials such Lucite or Mylar as sheet 10. Membrane 16 is bonded to sheet 10 with a suitable adhesive. I have used, for example, "Epoxy 220", made by Hughes Associates, Excelsior, Minn.

Cutouts 12, 13 and 14 are filled with a layer of an electrophoretic medium having a typical thickness of 0.25 mm. I prefer agarose gel as electrophoretic medium. The thickness of the layer of the electrophoretic medium and the thickness of sheet 10 may be identical so that the upper edges of the layer and of sheet 10 are at the same level. The layer of the electrophoretic medium may contain sample wells 18 – 20 which are formed by commonly known methods. Sheet 10 may also carry markers 22 – 24 which are used to actuate a densitometer to scan the completed electropherograms. Markers 22 – 24 may be either opaque to trigger an optical signal or they may be small means to actuate mechanical sensing switches. Each cutout, filled with the electrophroetic medium, may also be used for the electrophoresis of more than one sample, with a sample well being provided for each sample. The number of three cutouts in each plate is just given as example. There may be more or fewer cutouts per plate. When it is desired to measure the absorption of ultraviolet light caused by the presence of protein fractions by measuring the transmittance of light through the membrane and the electrophoretic medium, I prefer to use agarose gel made up with buffer solutions of low ultraviolet light absorption. Such buffers are commonly known.

It should be noted that the electrophoretic migration on the plates proceeds in the electrophoretic medium supported only by the thin membrane 16, but not by sheet 10. I have found that this feature provides for the excellent sharpness of the separations. It also provides for a method of directly measuring the absorption of ultraviolet light through the electrophoretic medium when membrane 16 is chosen to have a minimum absorption of ultraviolet light. The "Saran" membranes mentioned above are especially suited for this purpose.

Figure 2:
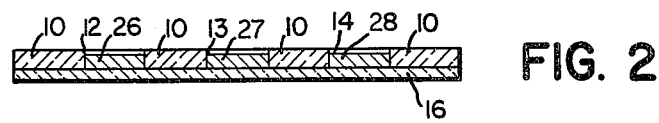
FIG. 2 is a view in cross section of the plate shown in FIG. 1.

FIG. 2 which is a cross sectional view of FIG. 1 shows the layers of the electrophoretic medium, 26, 27, and 28. They are confined by plastic sheet 10 and membrane 16.

Figure 3:
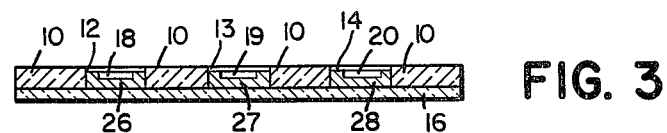
FIG. 3 is a cross sectional view of the plate shown in FIG. 1.

FIG. 3 is a cross sectional view of FIG. 1, showing sample wells 18, 19, and 20 in the layers of the electrophoretic medium 26, 27, and 28.

Figure 4:
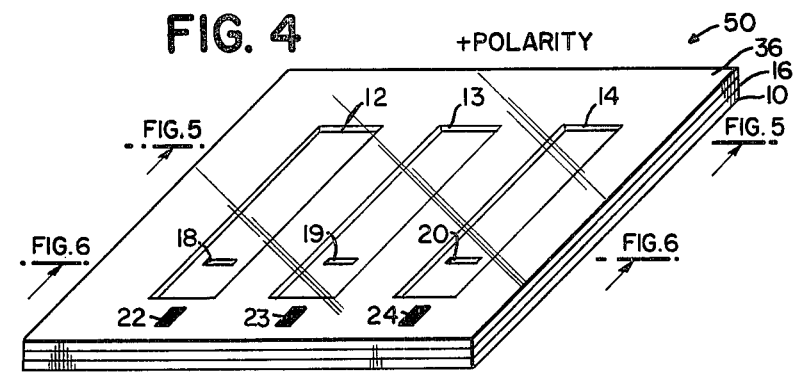
FIG. 4 is a view of another embodiment of the plate for performing electrophoretic separations thereon.

FIG. 4 shows another embodiment of an electrophoresis plate, generally indicated at 50. Membrane 16 is bonded to sheet 10. A continuous layer of the electrophoretic medium, 36, covers the membrane. Sample wells 18, 19, and 20 are provided in the layer of the electrophoretic medium.

Figure 5:
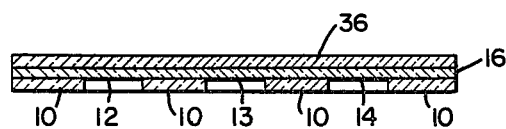
FIG. 5 is a cross sectional view of the plate shown in FIG. 4

FIG. 5 shows a cross sectional view of FIG. 4. Layer 36 is on top of membrane 10 having cutouts 12, 13, and 14.

Figure 6:
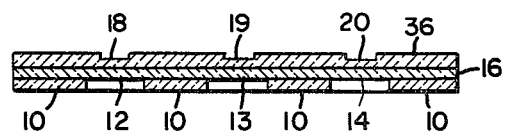
FIG. 6 is a view in cross section of the plate shown in FIG. 4

FIG. 6 shows a cross section of FIG. 4. Sample wells 18, 19, and 20 are shown in layer 36.

It should be noted that in the embodiment shown in FIG. 4, as well as in that shown in FIG. 1, the electrophoresis proceeds in the layer of electrophoretic medium supported only by membrane 16 and not by sheet 10.

It is understood that membrane 16 may be bonded to sheet 10 by suitable adhesives, by heat sealing, by mechanical means such as clamping or by other means.

The preferred electrophoretic medium is agarose since it provides for excellent separation and for high optical transmittance of ultraviolet light. However, other electrophoretic media such as agar gel or acrylamide gel may be used in the present structure. It is preferred to use gels which have no fluid characteristics. Such fluid characteristics appear when gels are used with low concentrations of the gelling agent. Agarose, for example, has fluid characteristics when below ~0.1 % concentration. I prefer to use agarose in concentrations higher than 0.2%, most preferably about 1% concentration by weight.

Figure 8:
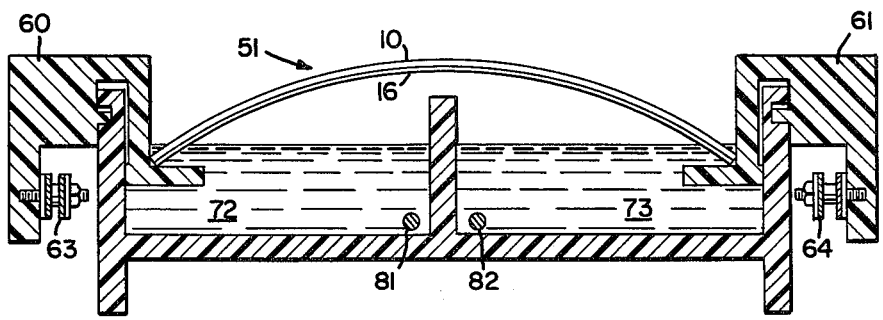
FIG. 8 is a cross sectional view of the apparatus shown in FIG. 7

In operation, the samples to be analyzed, typically 1 – 2 microliters, are introduced into sample wells 18 – 20 of plate 51. Electrolytic contact is established between plate and electrophoresis bath, with the polarity of the electric field in the direction as shown in FIG. 1. The electrophoresis plate may be bent as shown in FIG. 8 to establish contact. Other means of establishing contact by wicks etc. are known. The electric field is now applied until the fractions are separated. For the quantitative determination of the fractions I prefer optical measurements with ultraviolet light. However, other known means such as fluorometry or colorimetry may be used. It is common knowledge that proteins absorb ultraviolet light in several wavelength ranges, the strongest absorption being at about 205 nanometers. I prefer to use this wavelength range. Densitometers for scanning electrophoresis strips are known. The scanning is performed in the direction of the long axis of cutouts 12 – 14 which is also the direction of electrophoresis. The light beam is transmitted through membrane 16 and through layer 26 of the electrophoretic medium which is preferably agarose. The direct scanning of the layer 26 by measuring the light transmittance is an important aspect of the invention which is possible through the use of thin membrane 16 which is sufficiently transparent for ultraviolet light.

The electrophoresis plates may be used in the apparatus shown in FIG. 7. Plate 51 is held in a bent position by holders 61' and 60'. Holders 61' and 60' are connected to circular chains 63 and 64, respectively. Chain 64, being in the rear of the apparatus, cannot be seen in FIG. 7. Chain 63 is driven by sprocket 66 with a motor (not shown) which also drives chain 64 with a similar sprocket at the same speed. There is also shown another pair of holders, 60 and 61. In actual operation there will be a multitude of holder pairs all along chain 63. After application of samples on to plate 51 it is transported downwards into electrophoresis baths 72 and 73 so that the two opposite edges of plate 51 establish electrolytic contact. Bath 72 is connected to the negative outlet of a common electrophoresis power supply while bath 73 is connected to the positive outlet. The duration of the electrophoresis is determined by the speed of chain 63 and by the length of electrophoresis bath 72. After the appropriate time the plate is moved upward and out of the electrophoresis bath into densitometer 75. Densitometer 75 may be actuated by markers 24, 23, and 22 as they enter the densitometer. After scanning of the electropherograms plate 51 is discarded by automatically removing it from holders 61 and 60.

FIG. 8 shows a cross sectional view of FIG. 7. Plate 51 is resting in a bent position on holders 60 and 61 which are connected to chains 63 and 64, respectively. Plate 51 is contacting electrophoretic baths 72 and 73. Wire 81 is located in bath 72 to apply a negative voltage and wire 82 is located in bath 73 to apply a positive voltage from a power supply (not shown).

When agarose gel or another gel is used as the electrophoretic medium care must be taken to preserve the water content of the gel layer. The plate may be stored in an appropriate sealed container until use. Alternatively, the gel film may be dried after manufacture of the plate. The gel film is then restored by soaking it in a buffer solution before use.

It is understood that the foregoing detailed description is merely given by way of illustration and that many variations may be made therein without departing from the spirit of the invention. The "Abstract" given above is merely for the convenience of searchers and is not to be given any weight in defining the scope of the invention.

I claim:

1. A plate for performing electrophoretic separations, said plate comprising:
   a thin flexible membrane that is substantially transparent to ultraviolet radiation, said membrane being at least partially coated with an electrophoretic medium, and
   a support member supporting said membrane, there being at least one opening in said support member sufficiently large to allow electrophoretic separations and scanning by ultraviolet radiation of said electrophoretic medium to go unimpeded by said support member.

2. The plate of claim 1, wherein said electrophoretic medium has an absorbence of less than 0.7 for light of wavelengths between about 210 nanometers and about 240 nanometers.

3. The plate of claim 1, wherein said membrane has a thickness of less than about 0.1 millimeter.

4. The plate of claim 1, wherein the combinations of said membrane and said electrophoretic medium has a thickness less than about 1 millimeter.

5. The plate of claim 1, wherein said membrane is comprised of polyvinylidenechloride and said electrophoretic medium is comprised of agarose as a gelling agent.

6. The plate of claim 1, wherein said support member has a plurality of openings therein for multiple exposures of said membrane.

7. The plate of claim 1, wherein said electrophoretic medium has a recessed area therein for receipt of a sample to be analyzed.

8. The plate of claim 1, wherein said support member has a plurality of openings therein for multiple exposures of said electrophoretic medium.

9. The plate of claim 1, wherein said opening in said support member exposes said membrane.

10. The plate of claim 1, wherein said opening in said support member exposes said electrophoretic medium.

11. The plate of claim 1, wherein said electrophoretic medium is located in said opening.

12. The plate of claim 1, wherein different electrophoretic media are in contact with said membrane.

13. A plate for performing electrophoretic separations, said plate comprising:
a membrane which is sufficiently thin to be non self-supporting and transparent to ultraviolet radiation, said membrane being coated at least partially with an electrophoretic medium, and
a support member supporting said membrane, there being an opening in said support member sufficiently large to allow electrophoretic separations and scanning by ultraviolet radiation of said electrophoretic medium to go unimpeded by said support member.

14. The plate of claim 13, wherein said electrophoretic medium is located in said opening.

15. The plate of claim 14, wherein said electrophoretic medium has an area therein for containing a sample to be analyzed.

16. A plate for performing electrophoretic separations, said plate comprising:
a thin flexible membrane substantially transparent to ultraviolet radiation, said membrane having an electrophoretic medium thereon
a frame-like support member for supporting said membrane, said member having an opening therein across which said membrane extends, said opening being sufficiently large that said electrophoretic separations can occur in said medium and can be scanned by ultraviolet radiation, where said electrophoretic medium is on a side of said membrane remote from said support member.

17. A plate for performing electrophoretic separations, said plate comprising:
a thin flexible membrane substantially transparent to ultraviolet radiation, said membrane having an electrophoretic medium thereon,
a frame-like member for supporting said membrane, said member having an opening therein across which said membrane extends, said opening being sufficiently large that said electrophoretic separations can occur in said medium and can be scanned by ultraviolet radiation, where said support member has a plurality of openings therein, there being a membrane substantially transparent to ultraviolet radiation extending across said openings.

18. The plate of claim 17, where a single membrane extends across said plurality of openings.

19. A laminar structure for performing electrophoretic separations, comprising:
a generally planar support member having openings therein,
a thin non self-supporting membrane in contact with said support member, said membrane bridging said openings and being substantially parallel to said support member and supported thereby,
a coating of an electrophoretic medium on said membrane, said medium being accessible to incidence of ultraviolet radiation through said openings and through said membrane.

20. A plate for performing electrophoretic separation, said plate comprising:
a support member having a plurality of openings therein and including a surrounding frame portion, said support member being flexible and capable of being bent,
a thin flexible membrane bridging each said opening and held by said support member, said thin membrane being substantially transparent to ultraviolet radiation and having an electrophoretic medium in contact therewith, said ultraviolet radiation passing through said openings in said support member and scanning said electrophoretic medium to detect electrophoretic separations therein.

21. The plate of claim 20, wherein said electrophoretic medium has an absorbence of less than 0.7 for light of wavelengths between about 210 nanometers and about 240 nanometers, and wherein said membrane has a thickness of less than about 0.1 millimeter.

22. The plate of claim 21, wherein the combination of said membrane and said electrophoretic medium has a thickness less than about one millimeter.

23. A plate for performing electrophoretic separations, said plate comprising:
a thin membrane incapable of retaining a flat shape without support, and
a frame-like support member for supporting said membrane in a flat shape and including at least one opening which is bridged by said membrane, there being an electrophoretic medium in contact with the portion of said membrane bridging said opening, said membrane being sufficiently thin that it is substantially transparent to the radiation used to detect protein fractions in serum samples, wherein said radiation passes through said membrane and said electrophoretic medium during said scanning.

24. A plate for performing electrophoretic separations in a sample of body fluid, said plate comprising:
a thin membrane that is non self-supporting and substantially transparent to ultraviolet radiation, said membrane being at least partially coated with said sample and an electrophoretic medium,
a frame-like support member for supporting said membrane, there being an opening in said support member sufficiently large to allow electrophoretic separations to occur in said medium which can be scanned by ultraviolet radiation passing through said opening in said support member,
wherein said support member is sufficiently flexible to be bent into a curved shape for electrolytic contact at at least one edge thereof with an electrophoretic bath.

25. The plate of claim 24, where said support member is bent into a curved shape for electrolytic contact of opposing edges thereof with electrophoretic baths.

* * * * *